United States Patent [19]

Matsuo

[11] Patent Number: 4,799,387

[45] Date of Patent: Jan. 24, 1989

[54] AUTOMATIC ULTRASONIC TESTING METHOD

[75] Inventor: Junichi Matsuo, Chita, Japan

[73] Assignee: NGK Insulators, Ltd., Nagoya, Japan

[21] Appl. No.: 127,054

[22] Filed: Dec. 1, 1987

[30] Foreign Application Priority Data

Jan. 14, 1987 [JP] Japan .................................. 62-6973

[51] Int. Cl.$^4$ ............................................ G01N 29/04
[52] U.S. Cl. ......................................... 73/620; 73/629
[58] Field of Search ................. 73/600, 602, 609, 613, 73/620, 622, 627, 629

[56] References Cited

U.S. PATENT DOCUMENTS

3,940,952  3/1976  Mitchell ................................. 73/629
4,170,143  10/1979 Ries et al. ............................. 73/629

Primary Examiner—John Chapman
Attorney, Agent, or Firm—Parkhurst, Oliff & Berridge

[57] ABSTRACT

In an automatic ultrasonic testing method for automatically detecting an internal flaw of articles such as a solid-core station post insulator and a long-rod insulator in which ultrasonic noises are liable to be generated in ultrasonic testing waveform, use is made of a standard waveform having a plurality of maximum peak hold data in predetermined intervals at all the detecting points and obtained by detecting the normal article including the ultrasonic noises, with which ultrasonic testing waveforms of an article to be tested are compared. Therefore, it is possible to eliminate an instability of the ultrasonic testing waveform and to detect a flaw echo having a level lower than that of the ultrasonic noises.

3 Claims, 8 Drawing Sheets

Normal Article

FIG.5

Abnormal Article

FIG.6

Abnormal Article

FIG.7

Normal Article

FIG. 8

Normal Article

FIG. 9

After Processing
Waveforms of
Figs. 4 and 7

FIG.10

After Processing Waveform of Fig.5

FIG.11

After Proccessing Waveform of Fig.6

FIG. 12

After Processing
Waveform of Fig. 8

FIG. 13

Standard
Waveform

AUTOMATIC ULTRASONIC TESTING METHOD

BACKGROUND OF THE INVENTION

1. Related Art Statement

The present invention relates to an automatic ultrasonic testing method for automatically detecting internal flaws in articles such as solid-core station post insulators and long-rod insulators, in which ultrasonic noises are generated in ultrasonic testing waveforms.

2. Prior Art

Figure 4:
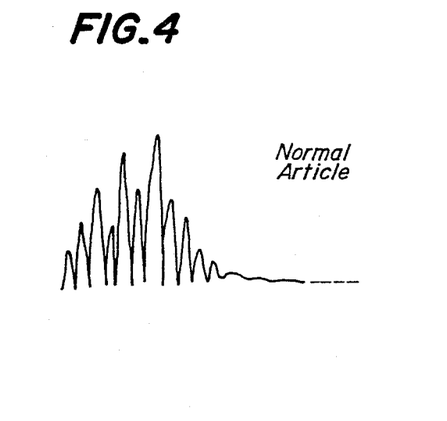
FIG. 4 is an ultrasonic testing waveform of a normal article.
Figure 6:
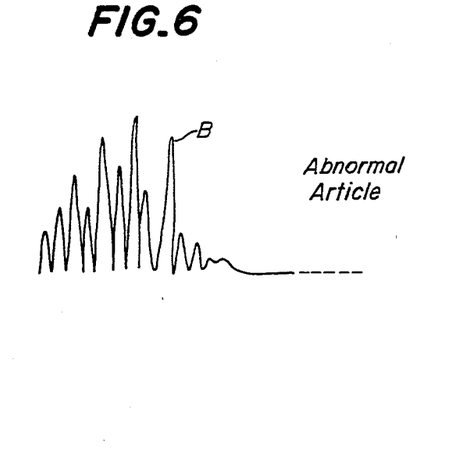
Figure 7:
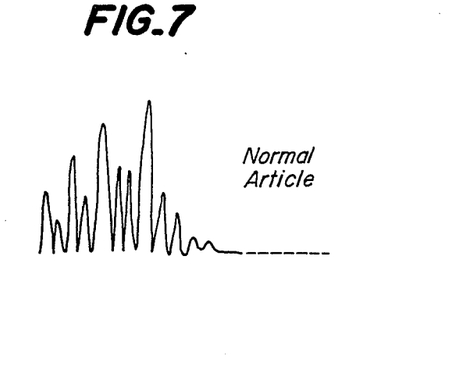
FIGS. 7 and 8 are an ultrasonic testing waveform of a normal article, respectively.
Figure 8:
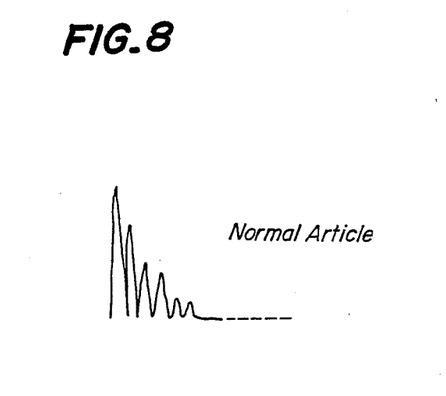

In the manufacturing steps of solid-core station post insulators or long-rod insulators, prior to assembling metal fittings with cement to upper and lower edges of a porcelain body, it is necessary to effect an ultrasonic test with respect to these upper and lower edges to detect any internal flaws. However, since the porcelain body always includes a plurality of porcelain shed portions, many echoes are generated due to the plurality of sheds. Therefore, even if the porcelain body is normal, ultrasonic noises such as those shown in FIGS. 4, 7 and 8 are generated in the ultrasonic testing waveforms. In this case, if the porcelain body has internal flaws, a flaw echo is shown by A in FIG. 5 or B in FIG. 6 in the ultrasonic testing waveform.

Usually, workers can easily visually detect the flaw echoes in the ultrasonic testing waveform, however, it is often very difficult to usually detect such flaw echoes by the naked eye, and thus it is likely that detection of the flaw echoes will vary from worker to worker. Therefore, it is required that detection of the flaw echoes be automated.

Figure 5:
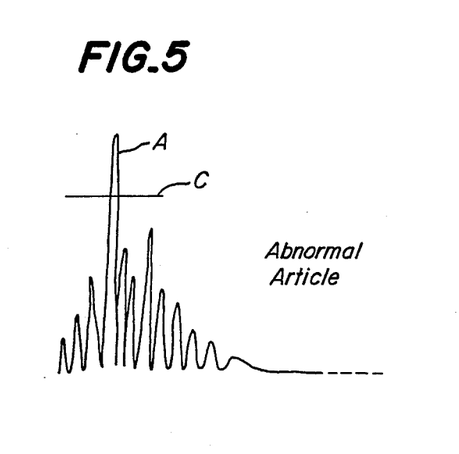
FIGS. 5 and 6 are an ultrasonic testing waveform including a flaw echo, respectively.

In a known normal automatic ultrasonic testing method, a slice level C shown in FIG. 5 is set at an arbitrary position in a wave image on a CRT, and an echo height beyond the slice level is detected as the flaw echo. However, in this method, since the slice level must be set beyond a maximum value of the ultrasonic noises as shown in FIG. 5, a flaw echo having an echo height below that of the ultrasonic noises as shown in FIG. 6 can not be detected.

Moreover, a method has been known in which a standard waveform including ultrasonic noises is set previously, and a flaw echo is automatically detected by comparing it with the standard waveform. However, in this method, it is very difficult to set the standard waveform because of the two reasons mentioned below.

First, since the ultrasonic noises change from the state shown in FIG. 4 to the state described in FIG. 7 as a result of a little variation in location of a probe, heights of adjacent pulses are partially shown in an inverse manner.

Second, since some positions generate ultrasonic noises such as shown in FIG. 8, it is extremely difficult to set the reasonable standard waveform.

Therefore, heretofore an automatic ultrasonic testing method has not been utilized for the articles such as insulators in which the ultrasonic noises are liable to be generated.

SUMMARY OF THE INVENTION

The present invention has for its object to eliminate the drawbacks mentioned above, and to provide an automatic ultrasonic testing method which can automatically detect a flaw echo having a level lower than a maximum level of ultrasonic noises.

According to the invention, an automatic ultrasonic testing method for automatically detecting an internal flaw of articles in which ultrasonic noises are generated in an ultrasonic testing waveform at a number of detecting points, wherein the method comprises the steps of (a) setting a standard waveform in a standard waveform memory by     effecting an ultrasonic test for a normal article having no internal flaws to obtain an ultrasonic testing waveform at a first detecting point,     dividing the ultrasonic testing waveform into a predetermined number of intervals along a time axis,     effecting a peak hold operation in all the intervals to obtain maximum data in every interval,     storing the maximum data in the standard waveform memory,     effecting the same peak hold operation at a next detecting point for all the intervals,     renewing the maximum data in the standard waveform memory by the peak hold data at the next detecting point if the data at the next detecting point is larger than that at the previous point, and     effecting the same processing steps for all the detecting points, (b) effecting the ultrasonic test for an article to be tested at the same detecting points as those for the standard waveform setting step to obtain the processed ultrasonic testing waveforms, (c) comparing the ultrasonic testing waveform before processing or the processed waveform with the standard waveform successively at all the detecting points, and (d) detecting the article to be tested as a normal one when a level of the ultrasonic testing waveform before processing or the processed waveform is not beyond that of the standard waveform at all the detecting points.

DESCRIPTION OF THE PREFERRED EMBODIMENTS

Figure 2:
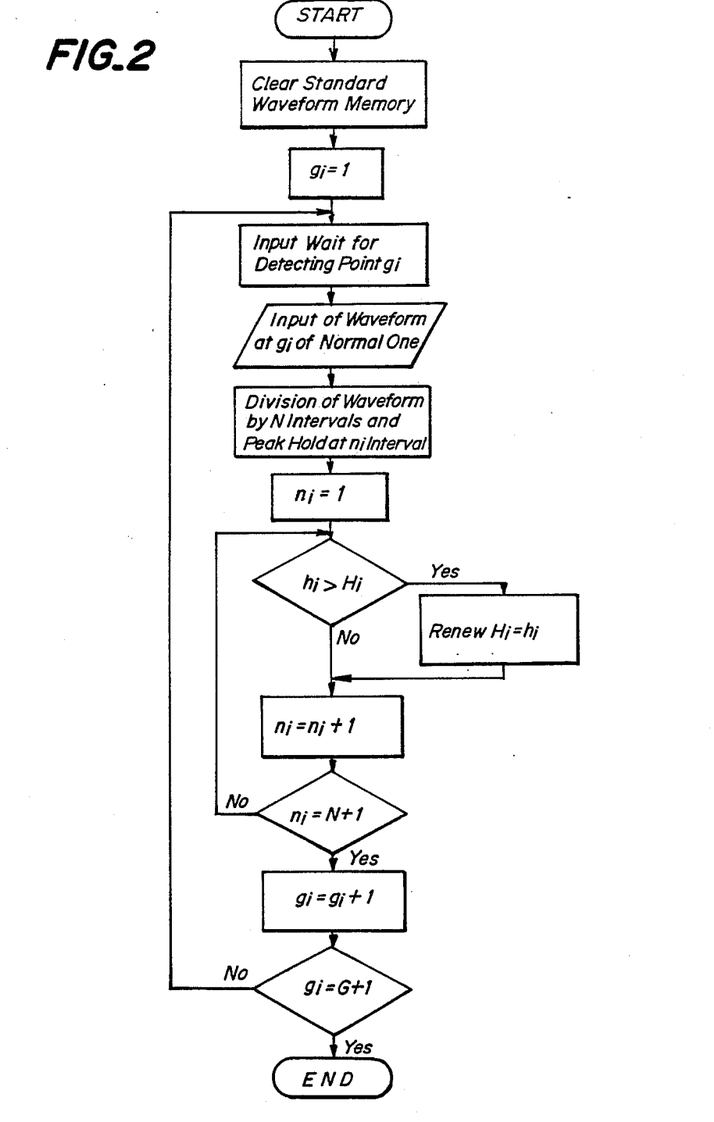
FIG. 2 is a flow chart illustrating a method of setting a standard waveform.
Figure 3:
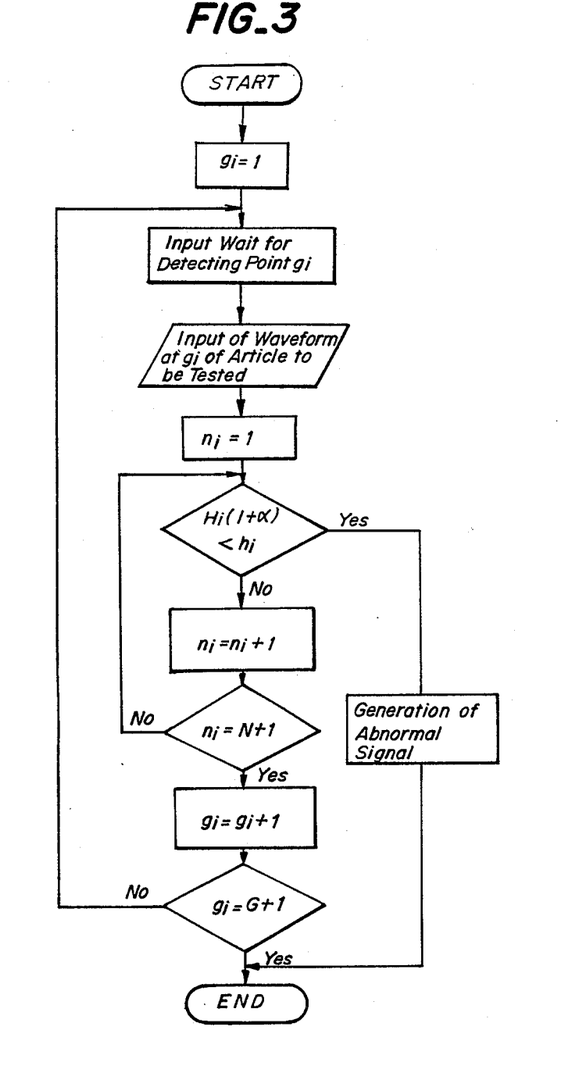
FIG. 3 is a flow chart depicting a method of detecting whether the article is good or not.

Hereinafter, the present invention will be explained in detail with reference to the drawings. In the drawings, FIG. 1 is a block diagram showing a system configuration according to the invention, FIG. 2 is a flow chart illustrating a method of setting a standard waveform, and FIG. 3 is a flow chart depicting a method of detecting whether the article is good or not.

Figure 1:
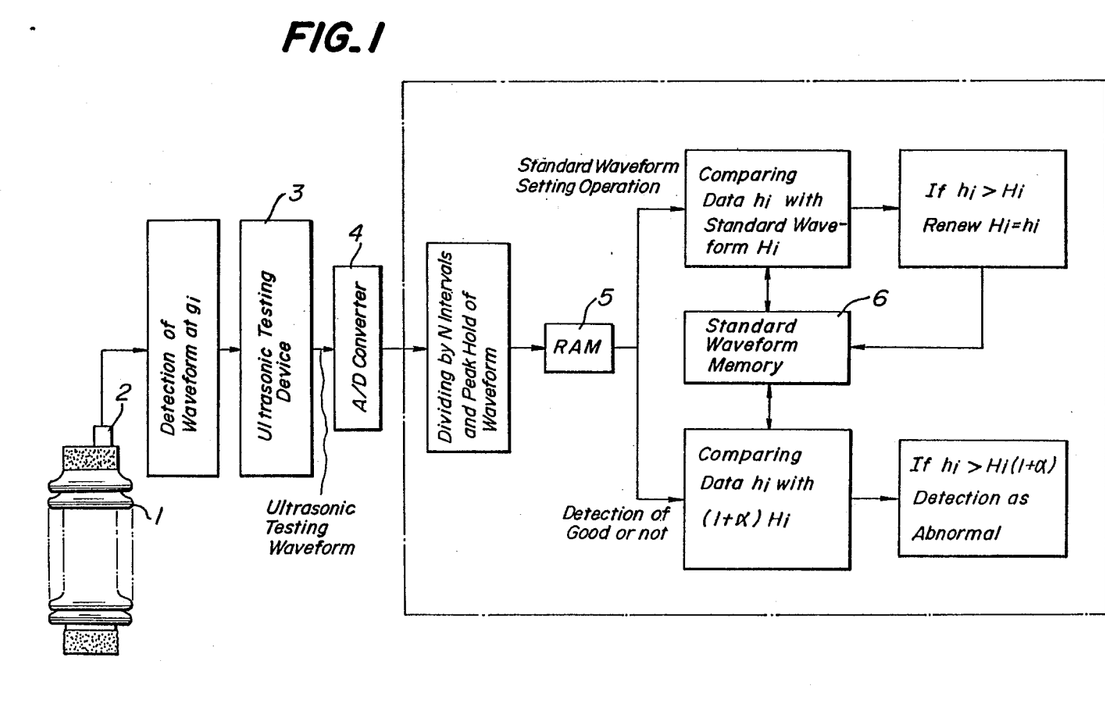
FIG. 1 is a block diagram showing a system configuration according to the invention.

In this embodiment, as shown in FIG. 1, a probe 2 is brought into contact with an upper surface of a normal article 1 such as a solid-core station post insulator having no internal flaws, and the probe 2 is moved successively on testing points $g_1, g_2, \ldots, g_i, \ldots, g_g$ to obtain outputs of ultrasonic testing waveforms of each points from an ultrasonic testing device. Then, the outputs of the ultrasonic testing device are converted into digital data by an A/D converter 4, and are processed by software in a microcomputer.

Figure 9:
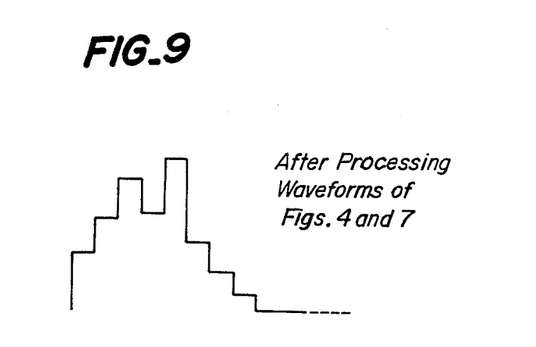
FIG. 9 is a digital waveform showing a result of conversion of the waveforms shown in FIGS. 4 and 7.
Figure 12:
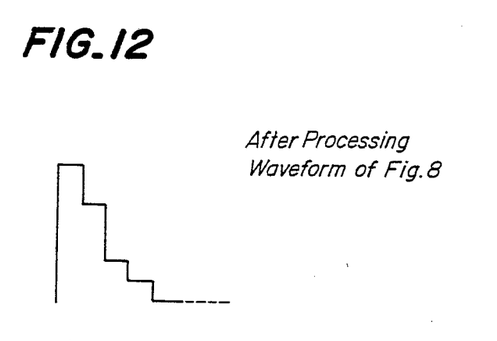
FIG. 12 is a digital waveform depicting a result of conversion of the waveform shown in FIG. 8.

At first, in the microcomputer, the waveform at point $g_1$ is divided into N intervals along a time axis, and peak hold data are obtained by holding a maximum value in each interval. Then, the peak hold data are stored in a RAM 5 and a standard waveform memory 6 as $H_1, \ldots, H_i, \ldots H_n$. In this case, the waveforms shown in FIGS. 4 and 7 including a partially inverse waveform can be converted into a waveform shown in FIG. 9 by setting a suitable N, and also the waveform shown in FIG. 8 can be converted into a waveform shown in FIG. 12.

Next, the same processing is performed for the waveform at point $g_2$ to obtain peak hold data $h_1, \ldots, h_i, \ldots h_n$ in each interval N. Then, the peak hold data $h_1, \ldots, h_i, \ldots h_n$ are compared with the stored data $H_1, \ldots, H_i, \ldots H_n$ in the standard waveform memory 6, respectively. In this case, if $h_k > H_k$, the stored data $H_k$ in the standard waveform memory 6 is renewed by $h_k$.

The same processing steps mentioned above are performed for the waveforms at the other points, successively. After the processings for all the points $g_1, \ldots, g_g$ are finished, the standard waveform is obtained in the standard waveform memory 6. In this case, the standard waveform can be shown in FIG. 13 which is constructed by the maximum data between the waveforms illustrated in FIG. 9 and FIG. 12. The method of setting the standard waveform mentioned above is shown in FIG. 2.

Figure 10:
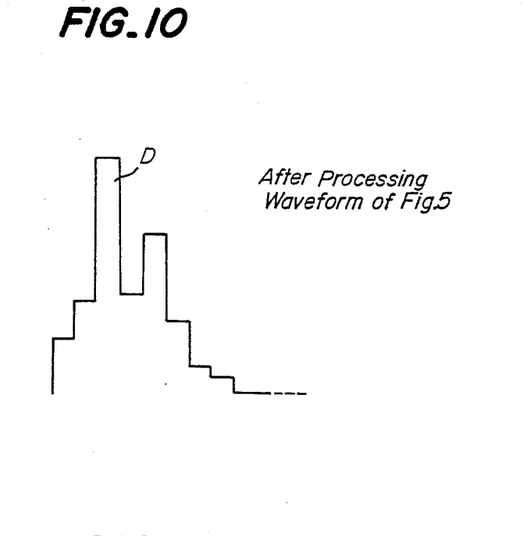
FIGS. 10 and 11 are digital waveforms illustrating results of conversions of the waveforms shown in FIGS. 5 and 6, respectively.
Figure 11:
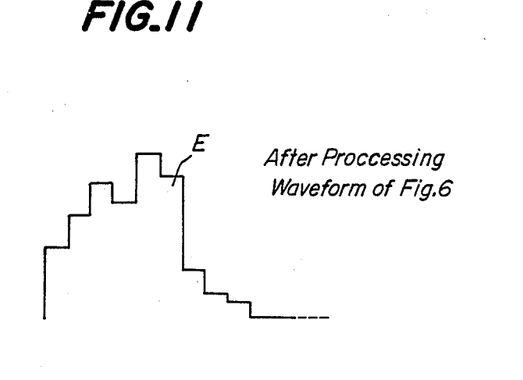
Figure 13:
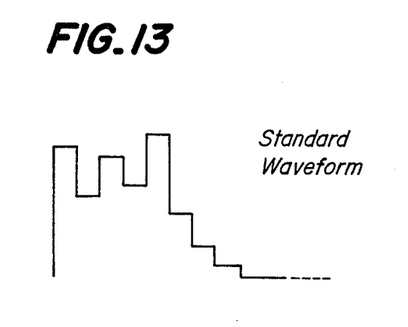
FIG. 13 is a synthetic standard waveform between the waveforms shown in FIG. 9 and FIG. 12.

After the setting operation of the standard waveform as shown in FIG. 13 is finished, the probe 2 is brought into contact with detecting points $g_i$ of an article to be tested to obtain the ultrasonic testing waveform of this article, and a detection of whether the article is good or not is performed by comparing the ultrasonic testing waveform before processing or processed waveform with the standard waveform. For example, if the processed waveform shown in FIG. 10 obtained by converting the waveform shown in FIG. 5 including the flaw echo is compared with the standard waveform shown in FIG. 13, an abnormal data D can be detected. Also, if the processed waveform of FIG. 11 obtained by converting the waveform shown in FIG. 6 including the flaw echo B is compared with the standard waveform shown in FIG. 13, an abnormal data E can be detected in the sixth interval. Contrary to this, no abnormal data beyond the standard waveform can be detected in the waveforms shown in FIGS. 9 and 12.

Moreover, if the ultrasonic waveform obtained from A/D converter 4 shown in FIG. 1 is directly compared with the standard waveform shown in FIG. 13, abnormal data, both A in FIG. 5 and B in FIG. 6, can also be detected.

In this manner, the detection of whether the article to be tested is good or not is performed theoretically, but actually for the sake of detection, use may be made of a standard waveform having data $(1+\alpha)$th larger than those of the standard waveform set in the manner mentioned above, wherein $0 < \alpha < 1$. That is to say, only in the case of $h_i > H_i(1+\alpha)$, the waveform is detected as abnormal. The method of detecting whether the article is good or not is shown in FIG. 3.

It should be noted that the comparing operation between the ultrasonic testing waveform of the article to be tested and the standard waveform may be performed by using a plurality of standard waveforms for respective groups each consisting of a predetermined number of peak hold data instead of using one standard waveform. As for a method of making groups, it is possible to use a group of peak hold data existent on a circle having a predetermined diameter. In this case, an improvement of the detection accuracy can be expected.

According to the invention, since the ultrasonic testing waveform is divided into N intervals along a time axis and the peak hold operation is performed for each interval, it is possible to eliminate an unstability of the ultrasonic testing waveform based on the inverse phenomena between heights of adjacent pulses generated by a little positional variation of the probe. Moreover, since the standard waveform is set by detecting the normal article including the ultrasonic noises, it is possible to detect a flaw echo having a level lower than that of the ultrasonic noises. Therefore, the present invention can be preferably applied for the automatic ultrasonic testing method for automatically detecting the internal flaw of articles such as the solid-core station post insulator and the long-rod insulator in which ultrasonic noises are generated in ultrasonic testing waveforms.

While the present invention has been disclosed in its preferred embodiments, it is to be understood that the invention is not limited to the precise disclosure contained herein, but may otherwise be embodied with various changes, modifications and improvements which may occur to those skilled in the art, without departing from the scope of the invention as defined in the appended claims.

What is claimed is:
1. An automatic ultrasonic testing method for automatically detecting an internal flaw of articles in which ultrasonic noises are generated in an ultrasonic testing waveform at a number of detecting points, said method comprising the steps of
  (a) setting a standard waveform in a standard waveform memory by
    effecting an ultrasonic test for a normal article having no internal flaws to obtain an ultrasonic testing waveform at a first detecting point,
    dividing the ultrasonic testing waveform into a predetermined number of intervals along a time axis,
    effecting a peak hold operation in all the intervals to obtain maximum data in every interval,
    storing the maximum data in the standard waveform memory,
    effecting the same peak hold operation at a next detecting point for all the intervals,
    renewing the maximum data in the standard waveform memory by the peak hold data at the next detecting point if the data at the next detecting point is larger than that at the previous point, and
    effecting the same processing steps for all the detecting points,
  (b) effecting the ultrasonic test for an article to be tested at the same detecting points as those for the standard waveform setting step to obtain ultrasonic testing waveforms,

(c) comparing the ultrasonic testing waveform for the tested article either before or after processing of the waveform with the standard waveform successively at all the detecting points, and (d) detecting the article to be tested as a normal one when a level of the ultrasonic testing waveform is not beyond that of the standard waveform at all the detecting points.

2. An automatic ultrasonic testing method according to claim 1, wherein said detecting points are divided into a plurality of groups, and a plurality of standard waveforms each corresponding to respective groups are used for the detection.

3. An automatic ultrasonic testing method according to claim 1, wherein use is made of a waveform whose level is $(1+\alpha)$th times larger than that of the standard waveform as the standard waveform wherein $0<\alpha<1$.

* * * * *